US 8,705,837 B2

(12) United States Patent
Michelsson et al.

(10) Patent No.: US 8,705,837 B2
(45) Date of Patent: Apr. 22, 2014

(54) METHOD FOR INSPECTION AND DETECTION OF DEFECTS ON SURFACES OF DISC-SHAPED OBJECTS AND COMPUTER SYSTEM WITH A SOFTWARE PRODUCT FOR CARRYING OUT THE METHOD

(75) Inventors: Detlef Michelsson, Wetzlar-Naunheim (DE); Daniel Skiera, Langgoens (DE)

(73) Assignee: KLA-Tencor MIE GmbH, Weilburg (DE)

( * ) Notice: Subject to any disclaimer, the term of this patent is extended or adjusted under 35 U.S.C. 154(b) by 252 days.

(21) Appl. No.: 13/293,169

(22) Filed: Nov. 10, 2011

(65) Prior Publication Data

US 2012/0163698 A1 Jun. 28, 2012

(30) Foreign Application Priority Data

Dec. 22, 2010 (DE) .......................... 10 2010 061 505

(51) Int. Cl.
*G06K 9/00* (2006.01)
*G06T 7/00* (2006.01)
*G06F 17/15* (2006.01)

(52) U.S. Cl.
CPC .............. *G06T 7/001* (2013.01); *G06F 17/153* (2013.01)
USPC ....................................................... 382/141

(58) Field of Classification Search
USPC ....................................................... 382/141
See application file for complete search history.

(56) References Cited

U.S. PATENT DOCUMENTS

| 5,212,677 | A | * | 5/1993 | Shimote et al. ............ 369/53.17 |
| 5,544,256 | A | * | 8/1996 | Brecher et al. ................ 382/149 |
| 5,777,729 | A | | 7/1998 | Aiyer et al. |
| 7,065,460 | B2 | | 6/2006 | Nishimura |
| 7,593,587 | B1 | * | 9/2009 | Rosario .......................... 382/263 |
| 2009/0161097 | A1 | * | 6/2009 | Friedrich et al. ........... 356/237.5 |

FOREIGN PATENT DOCUMENTS

| DE | 103 07 454 A1 | 9/2004 |
| DE | 103 31 686 A1 | 2/2005 |
| DE | 10 2004 031 721 A1 | 1/2006 |
| DE | 10 2007 039 982 B3 | 2/2009 |
| DE | 10 2006 042 956 B4 | 10/2009 |
| WO | 2010/124081 A1 | 10/2010 |

* cited by examiner

*Primary Examiner* — Hadi Akhavannik
(74) *Attorney, Agent, or Firm* — Patentbar International, P.C.

(57) ABSTRACT

An image (30) of a disc-shaped object (100) is recorded, wherein the entire surface (100$_O$) is captured with a plurality of fields (60). A difference image (31) is formed, by subtracting a reference from each field (60) of the surface (100$_O$) of the disc-shaped object (100), and subject to a color transformation, wherein by a suitable choice of transformation signals in one channel are maximized, while at the same time undesired variations, caused by production, of the fields (60) are moved to a different channel. That combination of transformation and detection channel is chosen for which the largest number of pixels of a field (60) with the defect to be found are located outside the spread of the pixels of the respective field (60) on the surface (100$_O$) of the respective disc-shaped object (100) from production and provide the largest signals for the defect.

23 Claims, 10 Drawing Sheets

METHOD FOR INSPECTION AND DETECTION OF DEFECTS ON SURFACES OF DISC-SHAPED OBJECTS AND COMPUTER SYSTEM WITH A SOFTWARE PRODUCT FOR CARRYING OUT THE METHOD

CROSS REFERENCE TO RELATED APPLICATIONS

This patent application claims priority of German Patent Application No. 10 2010 061 505.6, filed on Dec. 22, 2010, the application is incorporated herein by reference.

FIELD OF THE INVENTION

The present invention relates to a method for the inspection and detection of defects on surfaces of disc-shaped objects. The term "disc-shaped object" not only relates to wafers, but also to displays for flat-panel screens.

Furthermore the invention relates to a computer system with a software product, wherein the software product together with the computer system carries out an inspection and detection of defects on surfaces of disc-shaped objects.

BACKGROUND OF THE INVENTION

In semiconductor manufacturing wafers are sequentially treated in a plurality of process steps during the production process. With increasing density of integration the quality requirements in respect of the structures formed on the wafers increase. In order to monitor the quality of the formed structures during the production process and to potentially find defects, the requirements as to quality, precision, and reproducibility of the elements handling the wafer and of the process steps are correspondingly high. This means that in the production of a wafer with a plurality of process steps and a plurality of layers of photoresist to be applied a reliable and early detection of defects is particularly important. In the optical detection of defects also the systematic errors due to variations of thickness of the application of photoresist to the semiconductor wafers need to be detected reliably and reproducibly. Therein it shall be possible to mark only those locations on the semiconductor wafer, which actually contain an error, which eventually has a negative impact on the functionality of the respective DIE or chip.

The international patent application WO 2010/124081 A1 discloses a method for optimizing an optical inspection and production process of semiconductor elements. Herein preferentially color images of the objects to be examined are recorded. From these images a plurality of representations in different color spaces is generated. Each of these representations and the channels, or data, corresponding to these representations, are analyzed. Therein the analysis can be carried out separately or in combination with other channels, in order to find out which representation or which combination of representations, channels, or combination of channels or data or combinations of data, provide the most adequate representation, in order to therewith carry out the analysis with an optical inspection algorithm. Therein the process may be automatized with respect to the generation of the representations of the image and/or the individual or multiple analysis.

The German patent DE 10 2007 039 982 B3 discloses a method for the optical inspection and visualization of the optical measurements obtained from disc-shaped objects. For this first at least one image of the at least one disc-shaped object is recorded. From the at least one image recorded a plurality of optical measurements is generated. Then a result image is generated, wherein to an area of the surface of the disc-shaped object the optical measurements of which are within a pre-defined interval, a color or brightness value is assigned. The color or brightness value is chosen from a pre-defined palette. Eventually at least one imaging parameter is varied in dependence on the recorded and evaluated optical measurements and/or in dependence on a visual check of the result image by an operator.

The German patent DE 10 2006 042 956 B4 discloses a method for optical inspection and visualization of optical measurements obtained from disc-shaped objects. At least one image of the at least one disc-shaped object is recorded. A plurality of optical measurements is obtained from the at least one recorded image. Then a color value is assigned to each optical measurement. Therefrom a result image is generated, wherein a color value, selected from a pre-defined palette, is assigned to an area of the surface of the disc-shaped object the optical measurements of which are within a pre-defined interval.

The German patent application DE 103 07 454 A1 discloses a method, an apparatus, and a software for the inspection of surfaces of a semiconductor substrate. Furthermore a method and an apparatus for the production of a structured semiconductor substrate using such a method or such an apparatus, respectively, are disclosed. In the method an image is recorded for the optical inspection of the surface of a semiconductor substrate. The image comprises a plurality of pixels with at least three corresponding intensities of different wavelengths, referred to as color values. By a transformation into a color space spanned by the intensity and color coordinates, a frequency distribution of pixels with equal color coordinate values is calculated from the color values. The frequency distribution calculated in this way is used for a comparison with a second frequency distribution calculated in a corresponding manner or with a quantity derived therefrom. By this method only the statement can be made that there is a defect on the surface of the disc-shaped substrate. No statement regarding the location of the defect on the surface of the disc-shaped substrate can be made.

Macroscopic images of semiconductor wafers or of surfaces of disc-shaped substrates show that the homogeneity of the layers changes radially. In particular during the application of resist changed homogeneities arise in regions distant from the center of the wafer. If, as has been done up to now, a uniform sensitivity is used for the entire radius of the wafer for the evaluation of images of the wafers recorded, it happens that the deviations at the edge are detected always, defects in the interior (close to the center of the wafer), however, are not detected. If a high sensitivity is chosen in order to surely detect defects in homogeneous regions, then in the edge regions erroneous detections occur increasingly, because the inhomogeneous edge regions are not always to be classified as defects. In order to avoid this, the edge regions may be excluded entirely. Then, however, no real defects are found there. If a low sensitivity is chosen, then no erroneous detections occur any longer, defects in the homogeneous regions, however, cannot be found then.

The German patent application DE 103 31 686 A1 discloses a method for evaluating images recorded from wafers or other disc-shaped objects. After recording the image of at least one reference wafer the radial distribution of the measurements of the reference wafer is determined and displayed on a user interface as a radial homogeneity function. A sensitivity profile with radial dependence is changed taking into account the measured radial homogeneity function of the reference wafer. At least one parameter of the sensitivity profile is varied, so that a learned sensitivity profile is determined visually from the comparison with the radial homogeneity function. This method does not show an image of the entire wafer, based on which the image or the images are evaluated with respect to the defects, either.

The U.S. Pat. No. 7,065,460 discloses an apparatus and a method for the inspection of semiconductor elements. With the apparatus the electrical properties of the semiconductor product are examined. For representation on the display different colors are assigned to the results of the measurements.

Many prior art methods for inspecting the surface of a disc-shaped object for defects are known. Therein a wide variety of algorithms are used in order to visualize the defects in the images obtained from the measurements. Many of these methods, however, are not suitable for reliably detecting the defects. Eventually it depends on the experience of the operator to actually classify a defect found as a defect.

SUMMARY OF THE INVENTION

It is an object of the invention to provide a method for the inspection and detection of defects on the surface of disc-shaped objects, by which defects on the surface of disc-shaped objects can be inspected and detected, respectively, surely and reliably. The method according to the invention shall make it possible to define the correct transformation prescription, the correct detection channel, and a corresponding detection area, so that during a production lot of disc-shaped objects the defects possibly present on the disc-shaped objects can be detected surely and reliably in a reproducible fashion.

This object according to the invention is achieved by a method according to claim for inspecting and detecting defects on surfaces of disc-shaped objects, comprising the following steps:

capturing an image of the respective disc-shaped object, wherein the entire surface is captured with a plurality of fields;

deriving a defect-free reference of a pre-defined size from plural fields equal in size on the surface of the disc-shaped object;

generating a difference image of the surface of the disc-shaped object, wherein the derived reference is subtracted from each field on the surface of the disc-shaped object;

applying a color transformation to the difference image, wherein, by a suitable choice of transformation, signals in one channel are maximized, while undesired variations of the fields, caused by the production, are moved to a different channel;

evaluating the signals, wherein a mean value, a variance, a maximum value and a minimum value are determined for each field;

determining a distribution of the signals for each pixel of a field and a distribution of the signals for each defect to be examined, wherein the distribution is determined for each combination of transformation and detection channel used; and selecting that combination of transformation and detection channel, for which the largest number of pixels of a field with the defect to be found lie outside the spread of the pixels of the respective field on the surface of the respective disc-shaped object from production, and which results in the largest signals for the defect.

A further object of the invention is to provide a computer system with a software product, which makes it possible to inspect or detect, respectively, defects surely and reliably on the surface of disc-shaped objects. The software product according to the invention shall make it possible to define the correct transformation prescription, the correct detection channel, and a corresponding detection area, so that during a production lot of disc-shaped objects the defects possibly present on the disc-shaped objects can be detected surely and reliably in a reproducible fashion.

This object is achieved according to the invention by a computer system with a software product, wherein the software product together with the computer system carries out an inspection and detection of defects on surfaces of disc-shaped objects, wherein the software product comprises the following steps:

capturing an image of the respective disc-shaped object with a camera of a system, wherein the entire surface of the disc-shaped object is captured with a plurality of fields, and wherein an image capturing window of the camera essentially corresponds to the size of the field;

forming a defect-free reference of a pre-defined size from plural fields, equal in size, of the surface of the disc-shaped object;

generating a difference image of the surface of the disc-shaped object, wherein the formed reference is subtracted from every field of the surface of the disc-shaped object;

applying a color transformation to the difference image, wherein by a suitable choice of the transformation signals in one channel are maximized, while at the same time undesired variations, caused by production, of the fields are moved to a different channel;

evaluating the signals, wherein a mean value, a variance, a maximum value and a minimum value are determined for each field;

determining a distribution of the signals for each pixel of a field and a distribution of the signals for each defect to be examined, wherein the distribution is determined for each combination of transformation used and detection channel used; and selecting that combination of transformation and detection channel, for which the largest number of pixels of a field with the defect to be found are located outside the spread of the pixels of the respective field on the surface of the respective disc-shaped object from production, and which yields the largest signals for the defect.

For the method according to the invention first an image of the respective disc-shaped object is recorded. Therein the entire surface of the disc-shaped object is captured with a plurality of fields. Out of plural fields of equal size on the surface of the disc-shaped object a defect-free reference of a pre-defined size is formed. After the defect-free reference is available, a difference image of the surface of the disc-shaped object is generated. Therein the formed reference is subtracted from each field of the surface of the disc-shaped object. A color transformation is applied to the difference image obtained this way. By a suitable choice of transformation signals are maximized to one channel. At the same time undesired variations, caused by the production, of the fields are moved to a different channel. Finally the signals are evaluated, wherein a mean value, a variance, a maximum value and a minimum value are determined for each field. The distribution of the signals is determined for each pixel of a field. Likewise a distribution of the signals for each defect to be examined is determined. The distribution is determined for each combination of transformation used and transformation channel used. Eventually that combination of transformation and detection channel is selected which yields the largest number of pixels of a field with the defect to be found outside the spread of the pixels of the respective field on the surface of the respective disc-shaped object from production.

The fields on the surface of the disc-shaped object may be chosen such that the fields of a structured surface of the disc-shaped object at least contain a rational fraction of a DIE.

With the method according to the invention it is also possible to inspect the surface of a disc-shaped object, wherein the surface is an unstructured surface. Therein the fields are chosen such that for the unstructured surface of the disc-shaped object all fields to be examined are distributed in such a way that they cover the surface of the disc-shaped object and lie within a circumference of the disc-shaped object.

Via a user interface plural pixels may be combined into a detection value. In this way the pixel noise can be minimized and thus a choice between a spatial resolution and a noise suppression can be made. The larger the number of pixels combined into a detection value, the larger the noise suppression. If the number of pixels combined into a detection value is small, the spatial resolution increases. A user of the method according to the invention, by a suitable choice of the number of pixels combined into a detection value, thus can decide whether he wants to choose between more spatial resolution or more noise suppression. The differences to be formed are formed for n×m pixels of the respective field to be examined with the corresponding pixels of the respective reference. The resulting differences are summed up for each color channel separately.

The difference image generated this way may be subject to a normalization to an illumination intensity, in order to achieve an independence from the illumination intensity. To each pixel of the generated difference image a constant value is added, in order to be able to also represent negative values of the difference image.

The difference image is separated into individual channels, in order to obtain three different grey level images therefrom. A filter with a radial polynomial may be superimposed on a difference image.

A detection of a defect may be achieved by applying a threshold to the difference image. All locations in the difference image with values higher than the threshold are classified as a defect. The threshold is a function of the distance from a center of mass of the disc-shaped object.

On a structured surface of a disc-shaped object each field comprises plural different regions exhibiting different specificities of the defect. In each field it is determined for each region how strongly the signals for the fields from production vary. A mean value and a variance are formed for each field. In addition a minimum value and a maximum value are determined. For the fields containing the defect the values of the regions are determined separately. The distribution of the signals for the fields and of the regions is determined for each combination of transformation and detection channel. A detection of a defect is achieved by dividing the difference image of the respective field by the variance of the region in the respective field.

With the method according to the invention it is possible to evaluate defined defects on the surface of a disc-shaped object on the basis of a learning phase. By means of the defined defects it is possible to carry out the determination of the optimal combination of transformation and channel based on the signals of these defects. Therein that transformation is chosen for which the largest number of fields containing the defect lie outside the spread of the field from production and yield the largest defect signals.

It is also possible that the system is trained by trial or the experience of the operator in the learning phase. The operator then determines those fields in which defects are to be expected.

According to a further embodiment of the invention a morphological gradient is formed on the transformed difference image, so that changes of the signal can be evaluated.

The method according to the invention is used in the field of macroinspection. Prior art color detection was based on forming histograms in various color spaces. This kind of color detection was not or only to an insufficient degree able to detect the defects on the wafers from production. With the method according to the invention it is possible to better visualize the defects found. For visualizing the defects the difference image (Field-Difference-Image (FDI)) is used. To this now is added the difference image detection (Field-Difference-Detection (FDD)). With the difference image it was possible to visualize defects well, however only possible with difficulty to define the correct transformation prescription, the correct detection channel, and a suitable detection area.

In the macro module of the apparatus for the inspection of disc-shaped objects two fundamentally different detection principles are implemented. The first principle is pixel based detection, wherein pixel by pixel is compared with a partner for comparison and in case of a deviation a defect is generated. This detection is very well suited for the detection of very small high-contrast defects. The noise present in the brightness information of the pixel enters the detection fully. Therefore the threshold cannot be made arbitrarily small. The intensities of the color channels R, G, and B are processed independently of each other. The color information and the relation between the channels therefore is not relevant.

For color detection, on the contrary, the defect signal is generated on a larger area (color transformation, histogram generation, and center of mass calculation). Therefore the signal is less sensitive to noise, the spatial resolution, however, is very low. The color information is the decisive information.

Difference image detection (FDD) is a compromise trying to combine the strengths of both detections. In order to minimize the pixel noise plural pixels (4, 9, 16, 25, or more) are combined to a detection value. The number of pixels to be combined can be chosen via a user-interface. Thus it is possible to choose between spatial resolution and noise suppression. Before the proper detection can start, a local reference is calculated. For it a defect-free reference is formed from plural "equal" areas on the surface of the wafer by forming the median. This reference exhibits full pixel resolution. In order to generate the difference image for n×m pixels the differences of the pixels of the detection field with the corresponding pixels of the reference are formed. The differences are summed up separately for each color channel R, G, and B, and in the ideal case an RGB image results having the value {0, 0, 0}. As the signals usually are not very large, a rescaling by multiplication is done. For better representation the number 128 is added, in order to also be able to represent negative values as image. Next, a color transformation is done. By a suitable choice of color transformation the signals in one channel can be maximized, while the undesired variations from production are moved into a different channel. By normalization to the intensity also an independence from the illumination intensity is achievable.

Subsequently the channels in the difference image (color) are separated, and three greylevel images result.

The difference image is capable of visualizing the locations of the defects. However, in order to arrive at a usable result the signals still have to be evaluated. The simplest possibility is applying a threshold. All positions the values of which are larger than the threshold are classified as defects. This approach, however, is only suitable for unstructured wafers or if only a "cell area" of memory is considered. If the entire DIE of a structured wafer is to be examined, it is realized that different regions of the DIE exhibit different specificities of the defect. Furthermore it can be seen that the normal process fluctuations occurring during the production of semiconductor substrates or wafers, respectively, are imaged differently within a DIE.

For this reason the difference image detection uses a model in which is determined, for each field or DIE, how strongly the signals vary for normal production DIEs (POR). The mean value and the variance are determined for each region. In addition a minimum value and a maximum value are determined. For the DIEs affected by a defect (DOI) the values of the regions are captured separately. As the signals are different for different color transformations and choice of detection channel, the distribution of the signals for the production-DIEs and the signals for the DIE exhibiting the defect are determined for each combination of transformation and detection channel.

The difference image detection has the disadvantage that only if a wafer with defined defects in specific DIEs is available in the learning phase, the optimal transformation and channel combination can be found. If such a wafer is not available, the detection can only be optimally trained by trial or by experience. But even in this case the spread of the production DIEs is always taken into account.

In order to take into account the spread of the production process of wafers, plural wafers may be used for the determination of the spread of the production-DIEs. Also, a wafer may be added to an existing recipe as a production-DIE if erroneous detections on it are found.

A further extension of the difference image detection is that a morphological gradient is formed on the transformed difference image, similar to the pixel-based gradient detection. Thus not the signal itself is evaluated, but the change of this signal. This detection is particularly suited for the detection of very weak signals in homogeneous regions, in which the deviations of large extension, which are caused by the production process, have a perturbing effect on the detection.

BRIEF DESCRIPTION OF THE DRAWINGS

Below embodiments shall illustrate the invention and its advantages in more detail with reference to the accompanying figures.

FIG. 3$a$-3$c$ show the first section of the method according to the invention, wherein a difference image is generated.

FIG. 4$a$-4$c$ show the application of a color transformation to the difference image and the possibility of removing low frequency noise from the difference image.

FIG. 5$a$-5$c$ show the signals of the difference images, calculated from the various channels.

DETAILED DESCRIPTION OF THE PREFERRED EMBODIMENTS

Identical reference numerals are used for like elements of the invention or elements of like function. Furthermore, for the sake of clarity only reference numerals are shown in the individual figures which are necessary for the description of the respective figure.

Figure 1:
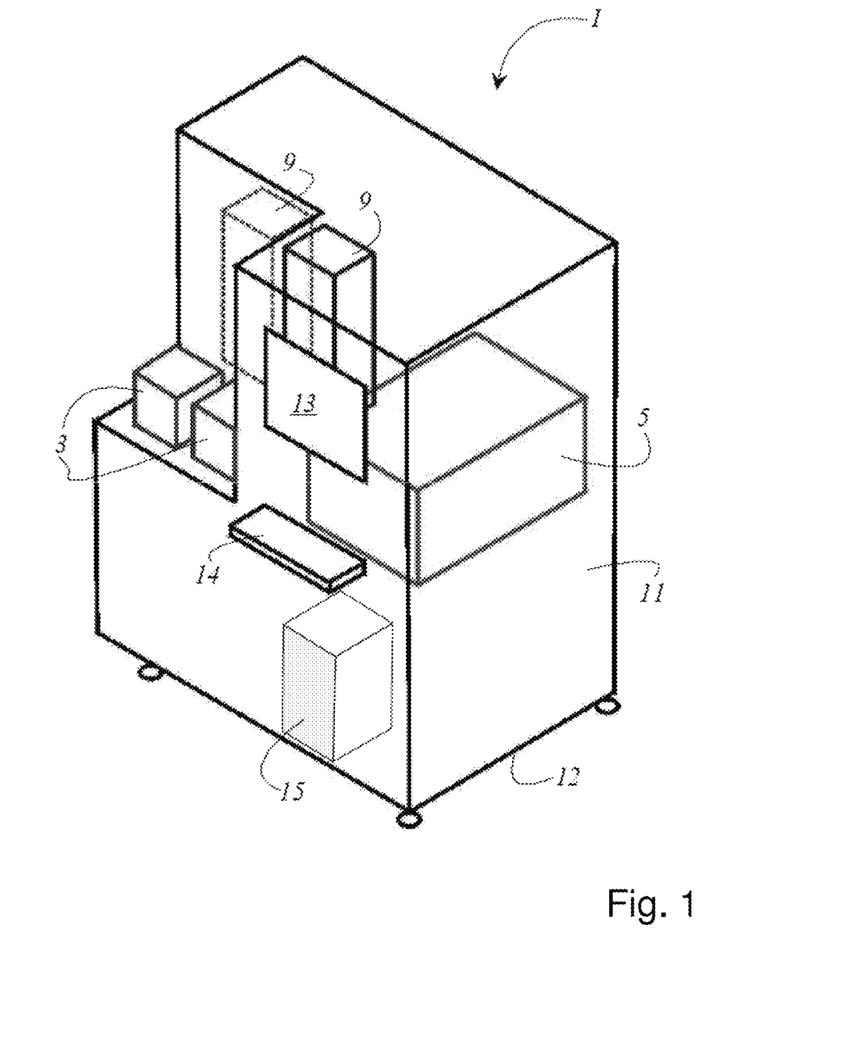
FIG. 1 shows a schematic representation of a system for the detection of errors or defects, respectively, on wafers or disc-shaped objects.

The schematic representation of FIG. 1 shows a system 1 for the inspection and detection of defects on wafers or disc-shaped objects 100. The system 1 for example has at least one cartridge element 3 for the semiconductor substrates, wafers, or disc-shaped objects. In a measuring unit 5 the images or image data, respectively, of the individual wafers are recorded. A transport apparatus 9 is provided between the at least one cartridge element 3 for the semiconductor substrates or wafers and the measuring unit 5. The system 1 is enclosed by a casing 11, wherein the casing defines a footprint 12. Furthermore a computer system 15 is integrated into the system 1, which receives the images or image data from the individual wafers measured and processes them. The system 1 is provided with a user interface 13 (display) and a keyboard 14. By means of the keyboard 14 the user can perform data input for the control of the system 1 or the input of parameters for improving the image data from the individual wafers. On the user interface 13 plural operator interfaces (BUI) are shown to the user of the system 1. The method according to the invention for the macroinspection of wafers is implemented in the system 1.

Figure 2:
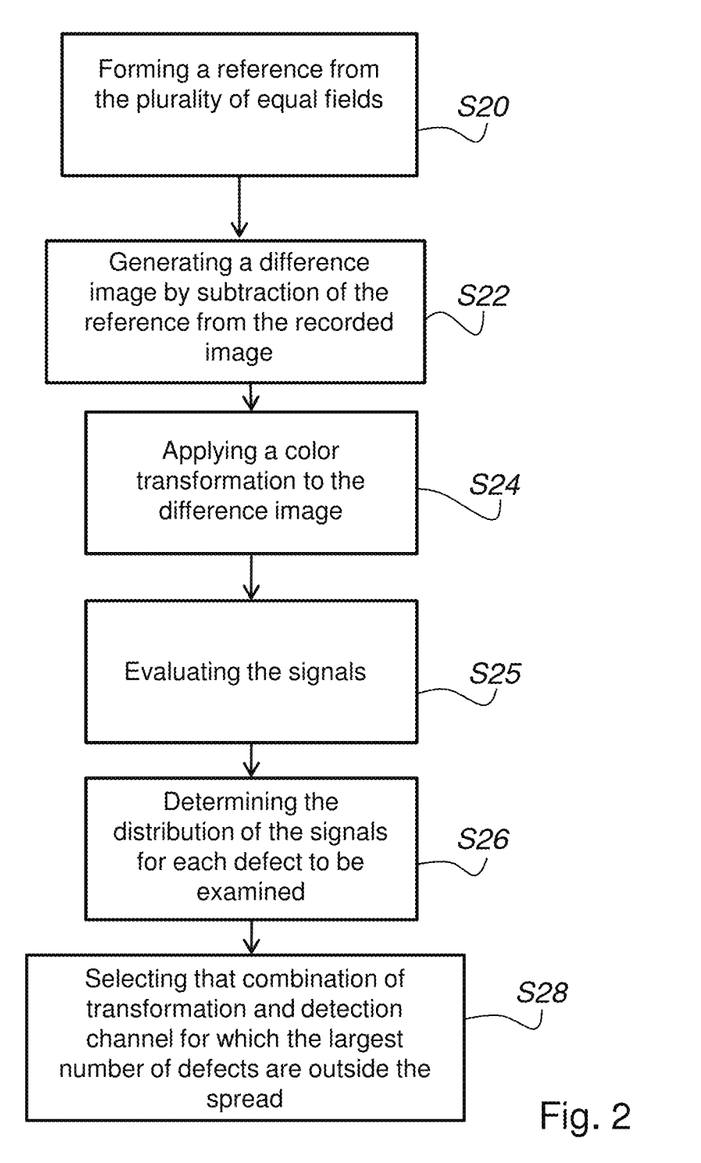
FIG. 2 shows a flow chart of the method according to the invention.
Figure 3A:
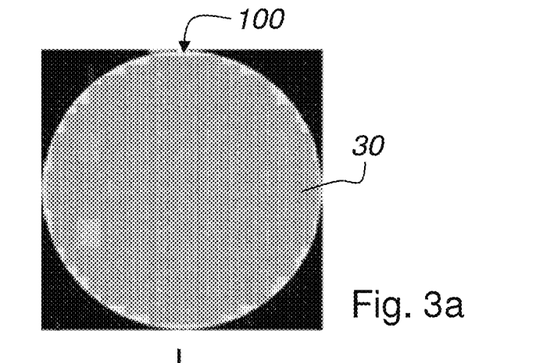
Figure 3B:
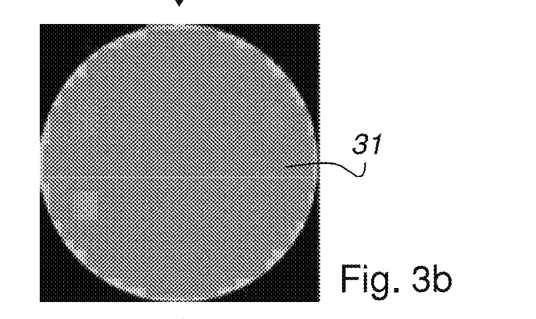
Figure 3C:
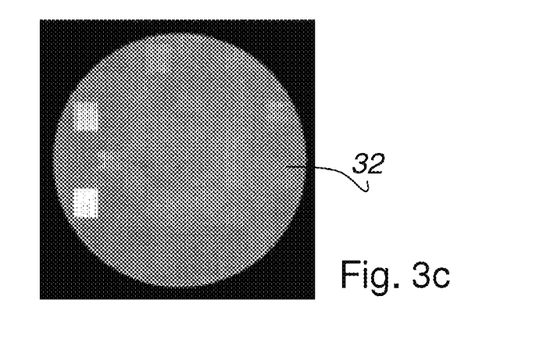

FIG. 2 shows a schematic representation of the flow chart of the method according to the invention, which in addition is shown graphically in FIGS. 3$a$ to 3$c$, 4$a$ to 4$c$, and 5$a$ to 5$c$ with reference to a disc-shaped object 100. The method according to the invention starts in a step S20, wherein a reference is determined from the plurality of equal fields 60 on the surface $100_O$ of a disc-shaped object 100. Subsequently, in a step S22, a difference image 31 is generated. This difference image 31 is obtained by subtracting the reference from the recorded image 30. The images 30 for example are obtained from wafers or semiconductor substrates from the production process for wafers.

In a subsequent step S24 a color transformation is applied to the difference image 31. Various color transformations are applied to the difference image 31. Each color transformation is evaluated in a subsequent step S25. Here the signals are evaluated in order to assess according to a pre-defined scheme whether the respective chosen color transformation or the respective chosen detection channel is suitable for achieving an as reliable as possible detection of the defects on the surface $100_O$ of the wafer. In a step S26 the distribution of the signals for each defect to be examined is determined. Eventually, in the last step S28, that combination of transformation and detection channel is selected, for which the largest number of defects is outside a pre-defined spread.

In the subsequent FIGS. 3$a$ to 3$c$, 4$a$ to 4$c$, and 5$a$ to 5$c$ it is shown graphically, how inspection and detection of defects on the surface of disc-shaped objects are carried out.

Although in the subsequent description only structured or unstructured wafers are used for describing the invention, this is not to be taken as a limitation of the invention.

FIG. 3a shows the recorded image 30 of the surface $100_O$ of a disc-shaped object 100. The image 30 of the disc-shaped object 100 (wafer) is represented as RGB image. Recording an image 30 of the respective disc-shaped object 100 is achieved by capturing the entire surface $100_O$ of the respective disc-shaped object 100 with a plurality of N fields. With a reference (not shown) a difference image 31 (see FIG. 3b) is generated. The reference is formed by forming a mean value from the plurality N of fields 60 equal in size, which thus is the defect-free reference. The reference is a field 60 of the surface $100_O$ of the disc-shaped object 100, which corresponds in size to the fields 60 through which the entire surface $100_O$ of a disc-shaped object 100 is captured. The difference image 31 is formed by subtracting the reference from each field of the surface $100_O$ of the disc-shaped object 100. The reference therein has the same size as a field on the surface $100_O$ of the disc-shaped object 100, wherein the entire surface $100_O$ of the disc-shaped object 100 is composed of a plurality of fields 60.

In the production process of the wafers a reference is obtained from a wafer. This reference then is applied to all wafers of the same type and the same production step. The inspection and detection of defects is done such that the reference is subtracted from the image of the surface $100_O$ captured with a plurality of N fields 60. Thus the difference image 31 of the surface $100_O$ of the wafer is obtained.

FIG. 3c shows a visual representation of the surface $100_O$ of the disc-shaped substrate 100, to which a histogram stretching 32 has been applied.

Figure 4A:
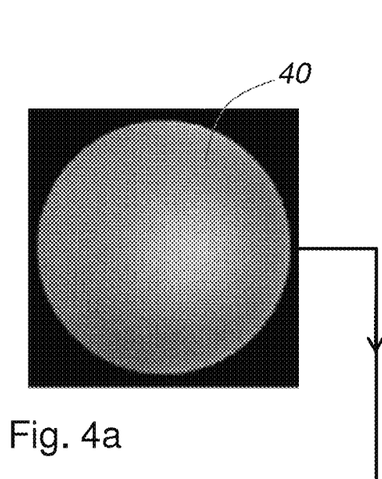

FIG. 4a shows the schematic representation of a radial polynomial 40, which may be applied to the difference image 31 in order to reduce low frequency noise. The radial polynomial 40 may for example be of fifth order.

Figure 4B:
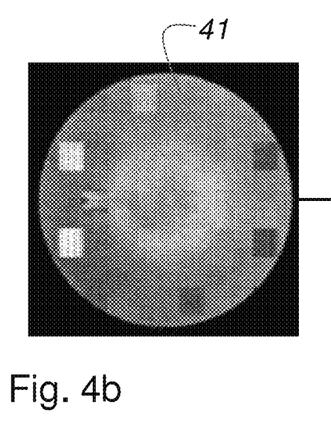

FIG. 4b shows the color transformation 41 of the difference image 31. Therein a first channel CH0 represents the addition of the red channel R, the blue channel B, and the green channel G.

$CH0=R+B+G$

A second channel CH1 represents the sum of the blue channel B and the green channel G, from which has been subtracted the red channel R.

$CH1=B+G-R$

A third channel CH2 represents the sum of the red channel R and the blue channel B, from which has been subtracted the green channel G.

$CH2=R+B-G$

Figure 4C:
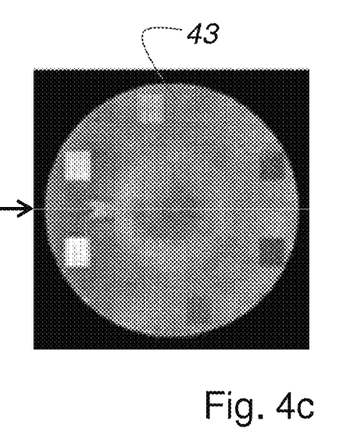

In FIG. 4c the difference image 43 is shown, from which the low frequency noise has been removed, too. Filtering with the low frequency noise is not a condition which is always applied in order to be able to better display the defects on the surface $100_O$ of the wafer or the disc-shaped substrate 100.

Figure 5A:
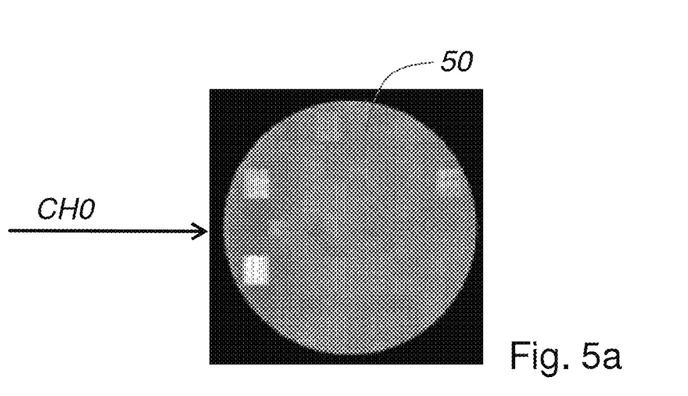
Figure 5B:
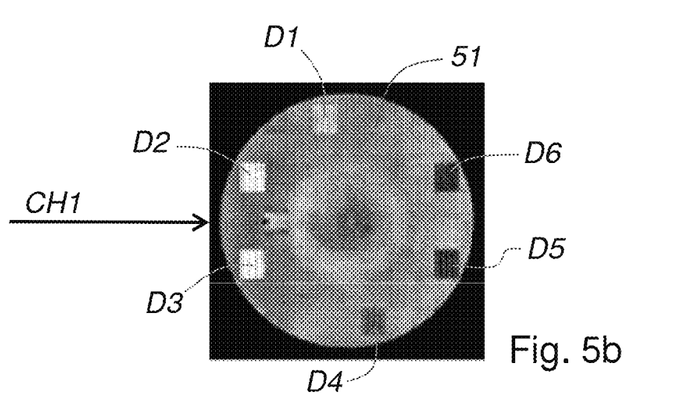
Figure 5C:
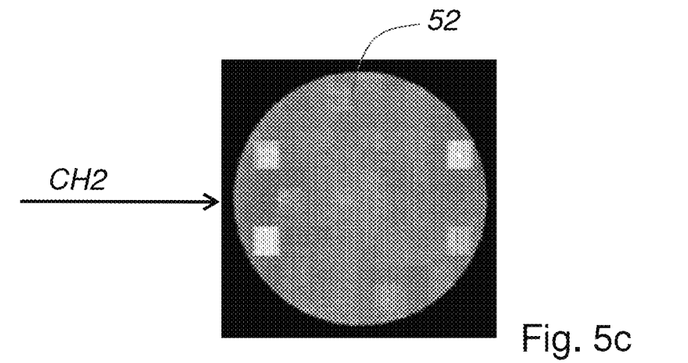

FIG. 5a shows the signal of the first channel CH0 in the visual representation 50 of the surface $100_O$ of the disc-shaped object 100. FIG. 5b shows the visual representation 51 of the surface $100_O$ of the disc-shaped object 100, according to the second channel CH1. FIG. 5c shows a visual representation 52 of the surface $100_O$ of the disc-shaped object 100, according to the third channel CH2. The signals in the different representations of FIG. 5a to FIG. 5c can only be calculated for separated signals of the red channel R, the blue channel B, and the green channel G. In the visual representation 51, shown in FIG. 5b, of the surface $100_O$ of the disc-shaped object 100 it is clear that for the second channel CH1 the detection of the defects D1 to D6 is unambiguous. Normally the defects D1 to D6 to be found are pre-defined defects on the surface $100_O$ of the disc-shaped object 100. For the detection during the production process that combination of transformation and channel is selected, for which the largest number of defects on the surface $100_O$ of the disc-shaped object 100 is detected.

Figure 6:
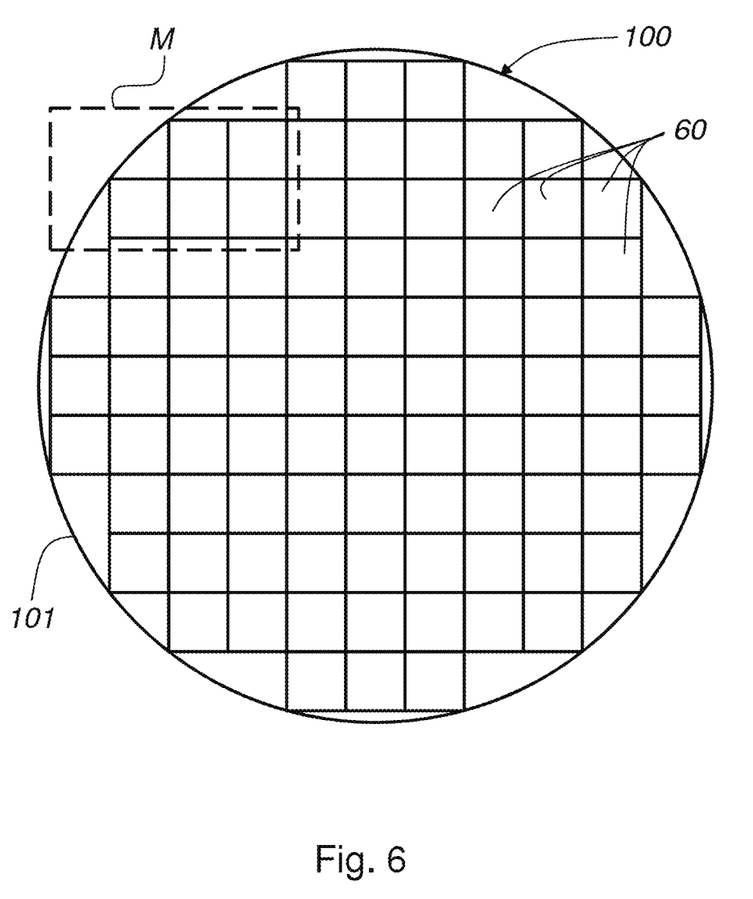
FIG. 6 shows a top view of a wafer in which plural fields of equal size cover the surface of the wafer.

FIG. 6 shows a schematic view of the surface $100_O$ of a disc-shaped object 100. The surface $100_O$ of the disc-shaped object 100 can be divided into a plurality of fields 60. With the plurality of fields 60 the entire surface $100_O$ of the disc-shaped object 100 can be recorded or optically captured. Each of the plurality of N fields 60 therein has the same size. With the method according to the invention both unstructured objects or wafers and structured objects or wafers can be inspected. In the case of structured objects or wafers the size of an individual field 60 is such that it corresponds to a rational fraction of a DIE (see FIG. 7) on the surface $100_O$ of the disc-shaped object 100. Each single field 60 on the surface of the disc-shaped object 100 may for example correspond to the image capturing window 22 of a camera 8, by which the entire surface $100_O$ of the disc-shaped object 100 within its circumference 101 is captured successively.

Figure 7:
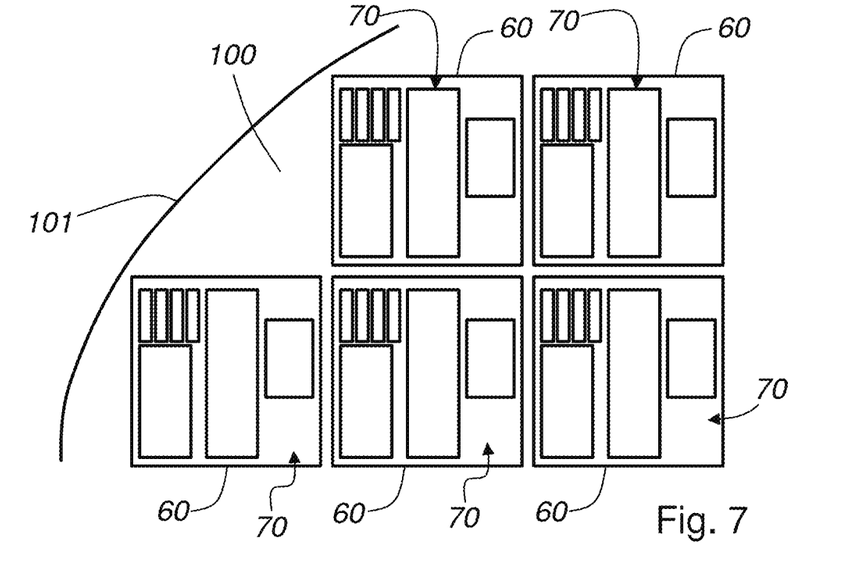
FIG. 7 shows the area marked in FIG. 6, in a magnified representation.

FIG. 7 shows an enlarged representation of the area dotted and marked M in FIG. 6. In the representation shown here each field 60 corresponds to a DIE 70 on the surface of the disc-shaped object 100. The fields 60 therein are arranged in such a way that they are located within the circumference 101 of the disc-shaped object 100.

Figure 8:
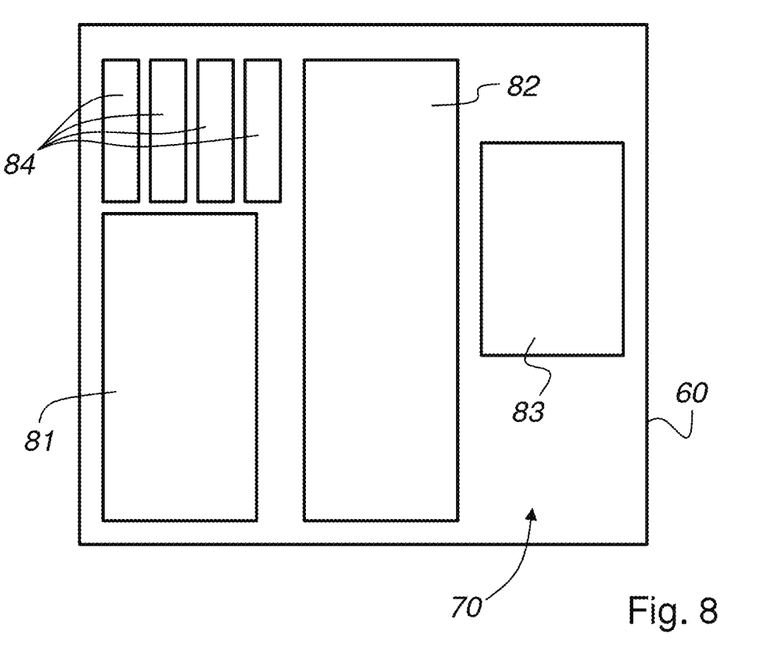
FIG. 8 shows a DIE on the surface of a disc-shaped substrate in enlarged and schematic representation.

FIG. 8 shows an enlarged representation of a DIE 70 captured with a single field 60. The DIE contains various regions 81, 82, 83, and 84, which are evaluated or weighted differently in the evaluation of the most ideal color transformation or channel combination. The difference image detection therein employs a model, in which for each region 81, 82, 83, and 84 of a DIE from production it is determined how strongly the signals for this production DIE vary. The mean value and the variance of the region are determined, which eventually enter the evaluation. The entire DIE 60 of the structured wafer thus encompasses various regions 81, 82, 83, and 84, which may exhibit different specificities of the defect. This is weighted with the corresponding weight in the assessment of the difference image detection.

Figure 9:
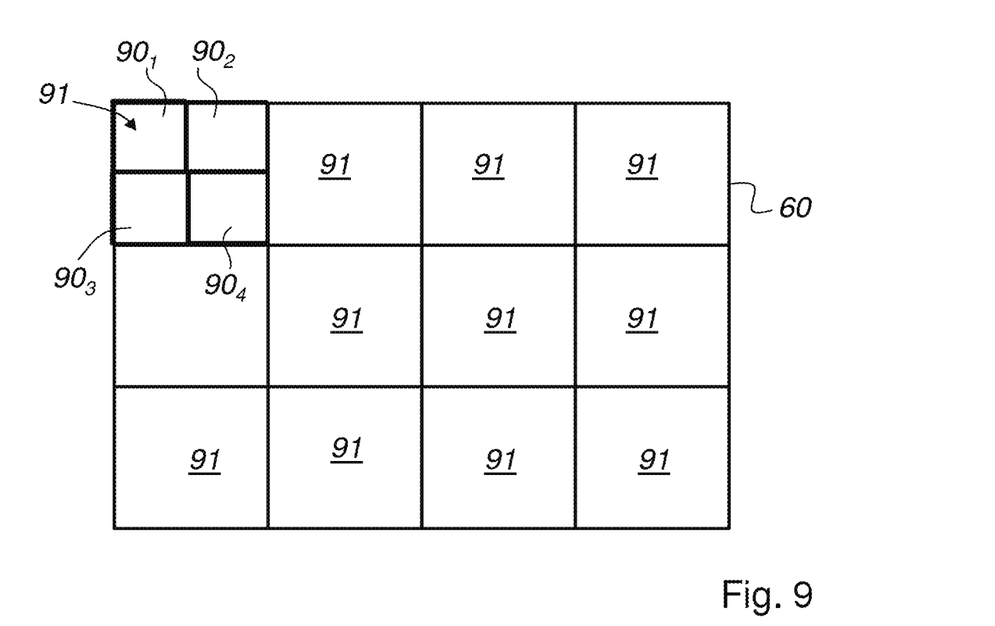
FIG. 9 shows the situation where four pixels are combined to a detection value for a field.

FIG. 9 shows a schematic view of a field 60. Here four pixels $90_1$, $90_2$, $90_3$, and $90_4$ are combined into a detection area 91. By combining plural pixels $90_1$, $90_2$, $90_3$, and $90_4$ to a detection area 91 thus the pixel noise within a field 60 is reduced. Via a user interface or display 13 of the system 1 the user can select the number of pixels $90_1$, $90_2$, $90_3$, and $90_4$, which are combined to a detection value or detection area 91, in order to minimize the pixel noise. In case of a small number of pixels $90_1$, $90_2$, $90_3$, and $90_4$ combined into a detection area 91 the user opts for a spatial resolution. In case of a large number of pixels $90_1$, $90_2$, $90_3$, and $90_4$ combined into a detection area 91, the user opts for a suppression of noise. Depending on the detection problem the user can choose between the spatial resolution and the noise suppression, in order to thus achieve an optimal detection result.

Figure 10:
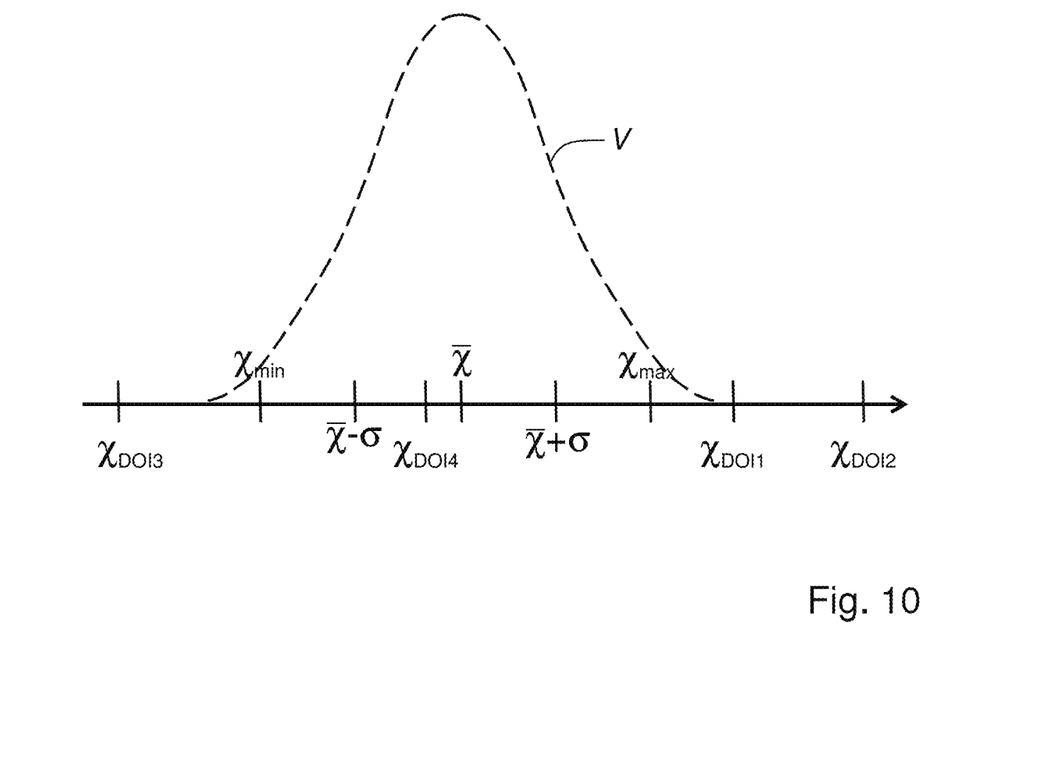
FIG. 10 shows an example based on which the suitable transformation/channel combination can be found.

FIG. 10 shows an example for the approach of the method according to the invention. Herein only one region of a DIE is considered, and only for one transformation/channel combination. For all production DIEs of the wafer or the disc-shaped object 100 a mean value $\chi$ and a variance $\sigma$ result. Likewise a minimum value $\chi_{min}$ and a maximum value $\chi_{max}$ can be assigned to the distribution V. For illustrating the calculation it is assumed that on the visual image of the disc-shaped object 100 there are four DIES (DOI1, DOI2, DOI3, DOI4) which represent a production DIE, which in each case exhibits an error or defect. The signals of the four production DIEs are referred to as $\chi_{DOI1}$, $\chi_{DOI2}$, $\chi_{DOI3}$, and $\chi_{DOI4}$. In the example shown in FIG. 10 the signal $\chi_{DOI1}$ of the first defect, the signal $\chi_{DOI2}$ of the second defect, and the signal ($\chi_{DOI3}$) of the third lie outside the spread of the production DIEs. The signal ($\chi_{DOI4}$) of the fourth defect, on the other hand, cannot be detected with the transformation/channel combination used here, as it lies within the spread. Normalizing the distance of the signal of a defect to the spread of the production DIES, the defect signal $S_{DOI}$ of the disc-shaped object (see equation 1) results.

$$S_{DOI} = \frac{\chi_{DOI} - \bar{X}}{\sigma} \qquad \text{Equation 1}$$

If the absolute value of a defect signal $S_{DOI}$ is assessed with a threshold, a detection which takes into account the product variance results. Areas which are very homogeneous on the entire wafer are assessed very strictly, i.e. even small differences are found here, while in regions with strong structure noise a less strict assessment is done.

Simultaneously in the learning phase the optimal transformation/channel combination can be determined by evaluating the signals of the defects. During the learning phase it is for example possible to do this with wafers or disc-shaped objects 100, on which defined defects are present. During the learning phase then that transformation is chosen for which for the largest number of disc-shaped objects 100 the defect lies outside the spread of the production DIEs and yields the largest defect signals. At the same time it is possible to automatically determine the "area of interest". Only areas for which the defect in the production DIE lies outside the spread of the production DIE can yield a meaningful signal. If, on the other hand, all defects lie within the spread of the production DIE, this disc-shaped object 100 does not yield a meaningful signal in the "Run"-phase on an unknown DIE, either.

The color transformation of the difference images can be an arbitrary transformation. Various color spaces, like for instance YUV, HSI, HSL, Lad, XYZ, etc. may be conceived of. Also arbitrary combinations of the channels, like for example $$a = \frac{R-G}{B}; b = \frac{B-G}{R}; c = \frac{G}{R+B}$$

are possible.

Currently 10 different transformations are provided in the system 1, the list can be extended arbitrarily, however, as existing recipes use that transformation, for which the defects yielded the optimal signal at the time of the learning phase.

In the learning phase a disc-shaped object 100 can be used which exhibits defined defects at defined locations. Specifically for the learning phase a wafer or disc-shaped object 100 is produced, for which the defects have been prepared at defined locations. During the learning phase that transformation/channel combination is used, for which the largest number of defects are found. This transformation/channel combination then is applied to all wafers or disc-shaped objects of the same type during production, in order to detect or inspect the defects during production.

Figure 11:
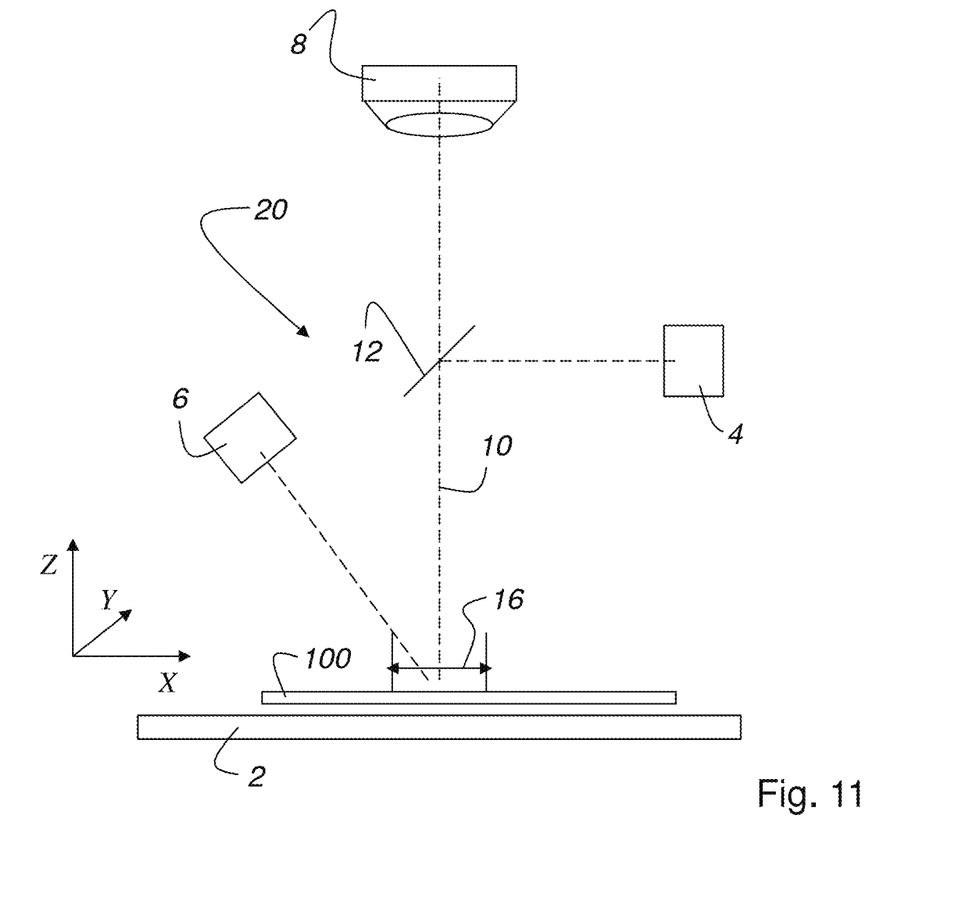
FIG. 11 shows a schematic optical setup for capturing an image of the surface of a disc-shaped object or of a wafer, respectively.

FIG. 11 shows a schematic representation of an optical apparatus 20 of the system 1 for recording an image of the surface of a disc-shaped object 100. The disc-shaped object 100 may be a wafer. The wafer therein is placed on a stage 2 movable in X-coordinate direction and in Y-coordinate direction. For illuminating the surface $100_O$ of the disc-shaped object 100 at least one top-light illumination system 4 and at least one dark-field illumination system 6 are provided. With the detector or a camera 8 the light from the surface $100_O$ of the disc-shaped object 100 can be converted to electric signals. In the embodiment shown here the light from the top-light illumination system 4 is coupled into the detection beam path 10 of the camera 8 by a beam splitter 12. In the embodiment shown here the entire surface $100_O$ of the disc-shaped object 100 is recorded in a so-called meander scan (see FIG. 12). Therein always a strip 16 of the part of the surface $100_O$ of the disc-shaped object 100 is recorded.

Figure 12:
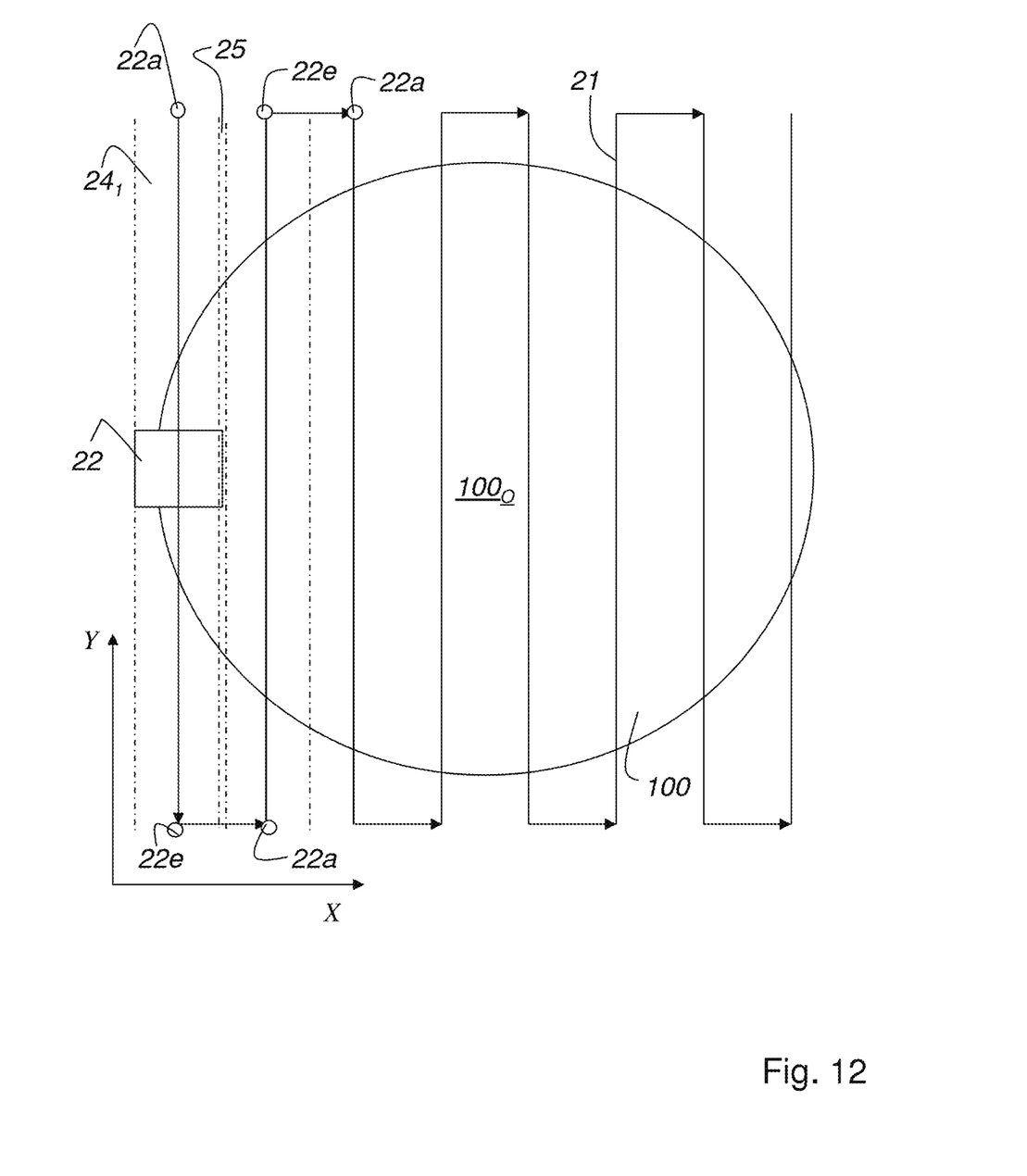
FIG. 12 shows a representation of capturing the surface of a wafer with an image capturing window of a camera.

FIG. 12 shows a top view of the surface $100_O$ of the disc-shaped object 100. The method by which the entire surface $100_O$ of the disc-shaped object 100 is recorded is shown. As an image capturing window 22 of the camera 8 is smaller than the diameter of the disc-shaped object 100, a so-called meander scan is necessary for recording the entire surface $100_O$ of the disc-shaped object 100. The image capturing window 22 captures part of the surface $100_O$. The image capturing window 22 now is moved in a meander 21 fashion across the surface $100_O$ of the disc-shaped object 100 in such a way that its entire surface $100_O$ is recorded. From a start position 22a either the camera 8 or the stage 2, on which the disc-shaped object 100 is positioned, is moved in Y-direction. Therein the image capturing window 22 of the camera 8 moves across a rectangular area $24_1$. The stage 2 is moved in Y-direction until the image capturing window 22 reaches the end point 22e. At the end point 22e the movement of the stage 2 in Y-direction is stopped. At the end point 22e a translation of the stage 2 or the camera 8 in X-coordinate direction is done. The translation in X-coordinate direction therein is not larger than the width of the image capturing window 22. It is obvious to a person skilled in the art that the translation in X-coordinate direction may also be somewhat smaller than the width of the image capturing window 22. In this case a small overlap region 25 results.

The present invention has been described with reference to preferred embodiments. Nonetheless modifications and alterations of the embodiments shown here can be made, without leaving the scope of the subsequent claims.

What is claimed is:

1. A method for inspecting and detecting defects on surfaces of disc-shaped objects, comprising the following steps:

capturing an image of the respective disc-shaped object, wherein the entire surface is captured with a plurality of fields;

deriving a defect-free reference of a pre-defined size from plural fields equal in size on the surface of the disc-shaped object;

generating a difference image of the surface of the disc-shaped object, wherein the derived reference is subtracted from each field on the surface of the disc-shaped object;

applying a color transformation to the difference image, wherein, by a suitable choice of transformation, signals in one channel are maximized, while undesired variations of the fields, caused by the production, are moved to a different channel;

evaluating the signals, wherein a mean value, a variance, a maximum value and a minimum value are determined for each field;

determining a distribution of the signals for each pixel of a field and a distribution of the signals for each defect to be examined, wherein the distribution is determined for each combination of transformation and detection channel used; and selecting that combination of transformation and detection channel, for which the largest number of pixels of a field with the defect to be found lie outside the spread of the pixels of the respective field on the surface of the respective disc-shaped object from production, and which results in the largest signals for the defect.

2. The method of claim 1, wherein the fields of the surface of the disc-shaped object are chosen such that the fields of a structured surface of the disc-shaped object contain at least a rational fraction of a DIE.

3. The method of claim 1, wherein the fields of the surface of the disc-shaped object are chosen such that for an unstructured surface of the disc-shaped object all fields to be examined are distributed such that they cover the surface of the disc-shaped object and lie within a circumference of the disc-shaped object.

4. The method of claim 1, wherein, via a user interface, plural pixels are combined into a detection area, in order to minimize pixel noise, and wherein a choice between spatial resolution and noise suppression is made.

5. The method of claim 1, wherein for n×m pixels differences of the pixels of the respective field to be examined and the corresponding pixels of the reference are formed, and wherein the differences are summed up separately for each color channel to form a difference image.

6. The method of claim 5, wherein the difference image formed is subject to a normalization to an illumination intensity, in order to achieve an independence from the illumination intensity.

7. The method of claim 6, wherein a constant value is added to each pixel of the difference image formed, in order to be able to represent also negative values of the difference image.

8. The method of claim 5, wherein the difference image is separated into individual channels, whence result three visual representations as greylevel images.

9. The method of claim 8, wherein a filter with a radial polynomial is superimposed on the difference image.

10. The method of claim 5, wherein a detection of a defect is achieved by applying a threshold to the difference image and classifying all positions in the difference image the values of which are larger than the threshold as defects.

11. The method of claim 10, wherein the threshold is a function of the distance from a center of mass of the disc-shaped object.

12. The method of claim 1, wherein in case of a structured surface of a disc-shaped object each field comprises plural different regions, exhibiting different specificities of the defect.

13. The method of claim 12, wherein for each region within the field it is determined how strong the signals for the fields from production vary, and wherein a mean value and the variance for each field and in addition a minimum and maximum value are determined.

14. The method of claim 13, wherein for the fields containing the defect the values of the regions are captured separately, and wherein the distribution of the signals for the fields and the regions is determined for each combination of transformation and detection channel.

15. The method of claim 12, wherein a detection of a defect is achieved by dividing the difference image of the respective field by the variance of the region in the respective field.

16. The method of claim 1, wherein in a learning phase based on a disc-shaped object with defined defects an evaluation of the signals of these defects and a determination of the optimal combination of transformation and channel are carried out, and wherein that transformation is chosen, for which the largest number of fields containing the defect are outside the spread of the field from production and provide the largest defect signals.

17. The method of claim 1, wherein in the learning phase an operator trains the detection of the system by trial or by experience, and determines the fields in which defects are to be expected.

18. The method of claim 1, wherein a morphological gradient is formed on the transformed difference image, so that changes of the signal are evaluated.

19. A computer system with a software product, wherein the software product together with the computer system carries out an inspection and detection of defects on surfaces of disc-shaped objects, wherein the software product comprises the following steps:

capturing an image of the respective disc-shaped object with a camera of a system, wherein the entire surface of the disc-shaped object is captured with a plurality of fields, and wherein an image capturing window of the camera essentially corresponds to the size of the field;

forming a defect-free reference of a pre-defined size from plural fields, equal in size, of the surface of the disc-shaped object;

generating a difference image of the surface of the disc-shaped object, wherein the formed reference is subtracted from every field of the surface of the disc-shaped object;

applying a color transformation to the difference image, wherein by a suitable choice of the transformation signals in one channel are maximized, while at the same time undesired variations, caused by production, of the fields are moved to a different channel;

evaluating the signals, wherein a mean value, a variance, a maximum value and a minimum value are determined for each field;

determining a distribution of the signals for each pixel of a field and a distribution of the signals for each defect to be examined, wherein the distribution is determined for each combination of transformation used and detection channel used; and selecting that combination of transformation and detection channel, for which the largest number of pixels of a field with the defect to be found are located outside the spread of the pixels of the respective field on the surface of the respective disc-shaped object from production, and which yields the largest signals for the defect.

20. The computer system of claim 19, wherein the fields of the surface of the disc-shaped object are chosen such that the fields of a structured surface of the disc-shaped object contain at least a rational fraction of a DIE.

21. The computer system according to claim 19, wherein, via a user interface of the system, plural pixels are combined into a detection area in order to minimize the pixel noise, and a choice between a spatial resolution and a noise suppression can be made.

22. The computer system according to claim 19, wherein for n×m pixels the differences of the pixels of the respective field to be examined and the corresponding pixels of the reference are formed, and wherein the differences are summed up separately for each color channel.

23. The computer system according to claim 19, wherein in a learning phase, based on a disc-shaped object with defined defects, an evaluation of the signals of these defects and the determination of the optimal combination of transformation and channel are carried out, and wherein that transformation is chosen, for which the largest number of fields containing the defect are located outside the spread of the field from production, and which yields the largest defect signals.

* * * * *